United States Patent [19]

Gates

[11] 4,037,472
[45] July 26, 1977

[54] EXPLOSION-PROOF FLOW SAMPLING APPARATUS

[75] Inventor: Wendall C. Gates, Santa Cruz, Calif.

[73] Assignee: Advanced Instrumentation Inc., Santa Cruz, Calif.

[21] Appl. No.: 723,820

[22] Filed: Sept. 16, 1976

[51] Int. Cl.² .............................................. G01N 1/14
[52] U.S. Cl. .................................. 73/421 B; 137/205; 222/205
[58] Field of Search .............. 73/421 B, 220; 137/205; 222/205

[56] References Cited

U.S. PATENT DOCUMENTS

| | | | |
|---|---|---|---|
| 3,727,464 | 4/1973 | Rutowski et al. | 73/421 B |
| 3,901,084 | 8/1975 | Brailsford | 73/421 B |
| 3,901,087 | 8/1975 | Fabritus | 73/421 B |
| 3,924,471 | 12/1975 | Singer | 73/421 B |

*Primary Examiner*—S. Clement Swisher
*Attorney, Agent, or Firm*—Owen, Wickersham & Erickson

[57] ABSTRACT

An apparatus for collecting samples of water from open flows is disclosed. The apparatus includes a controller, a quantimetric chamber and storage means, and provides for automatic collection and storage of liquid samples. The entire device is pneumatically operated and therefore suitable for use in explosive atmospheres.

21 Claims, 7 Drawing Figures

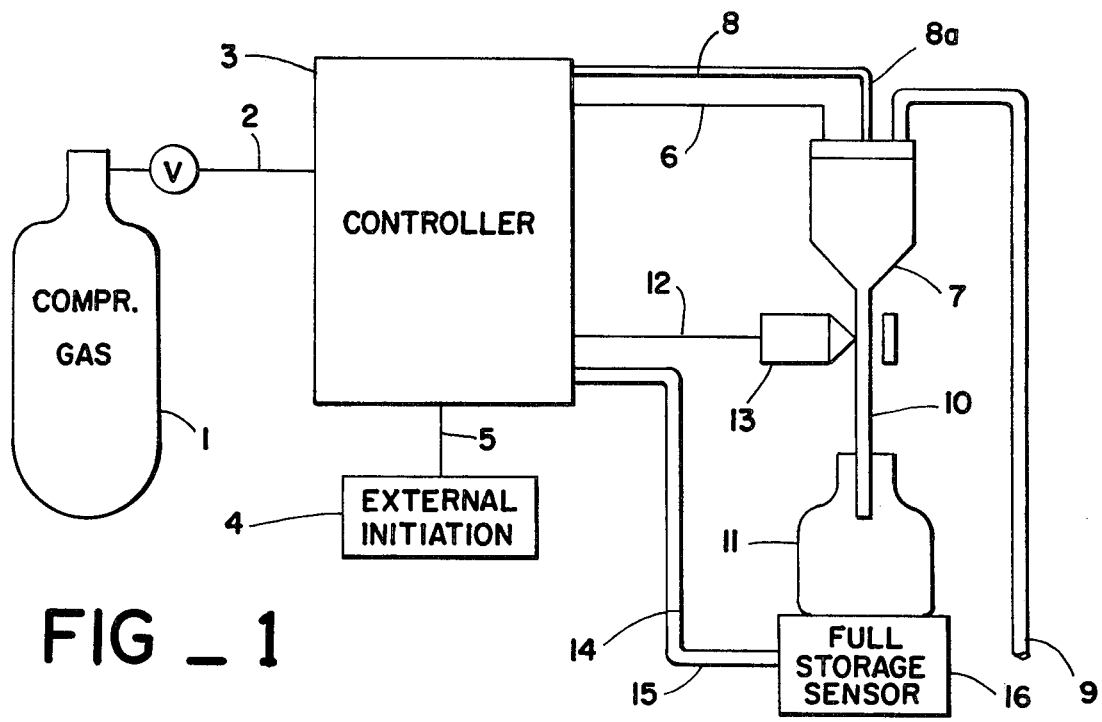
FIG _ 1
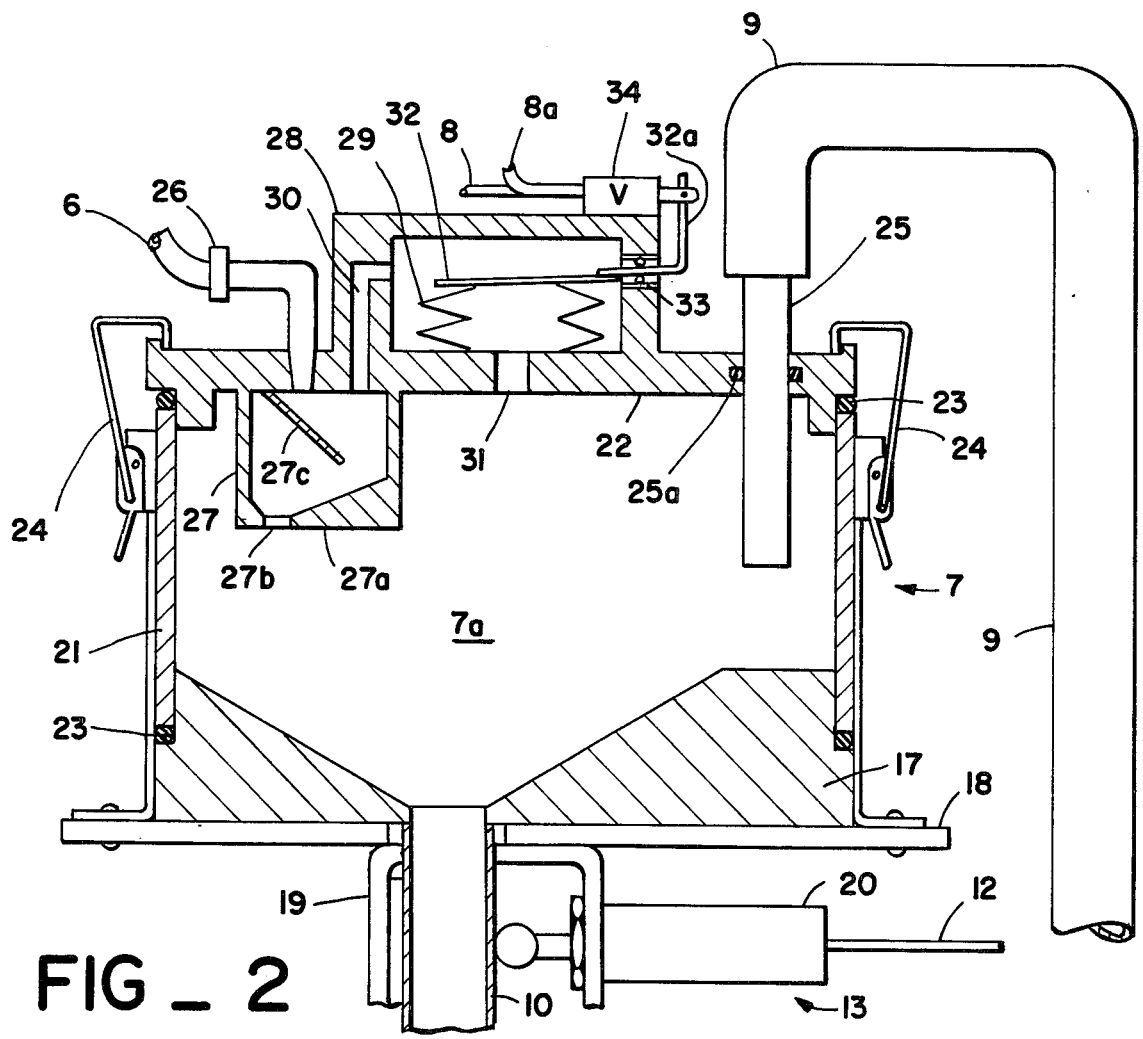
FIG _ 2

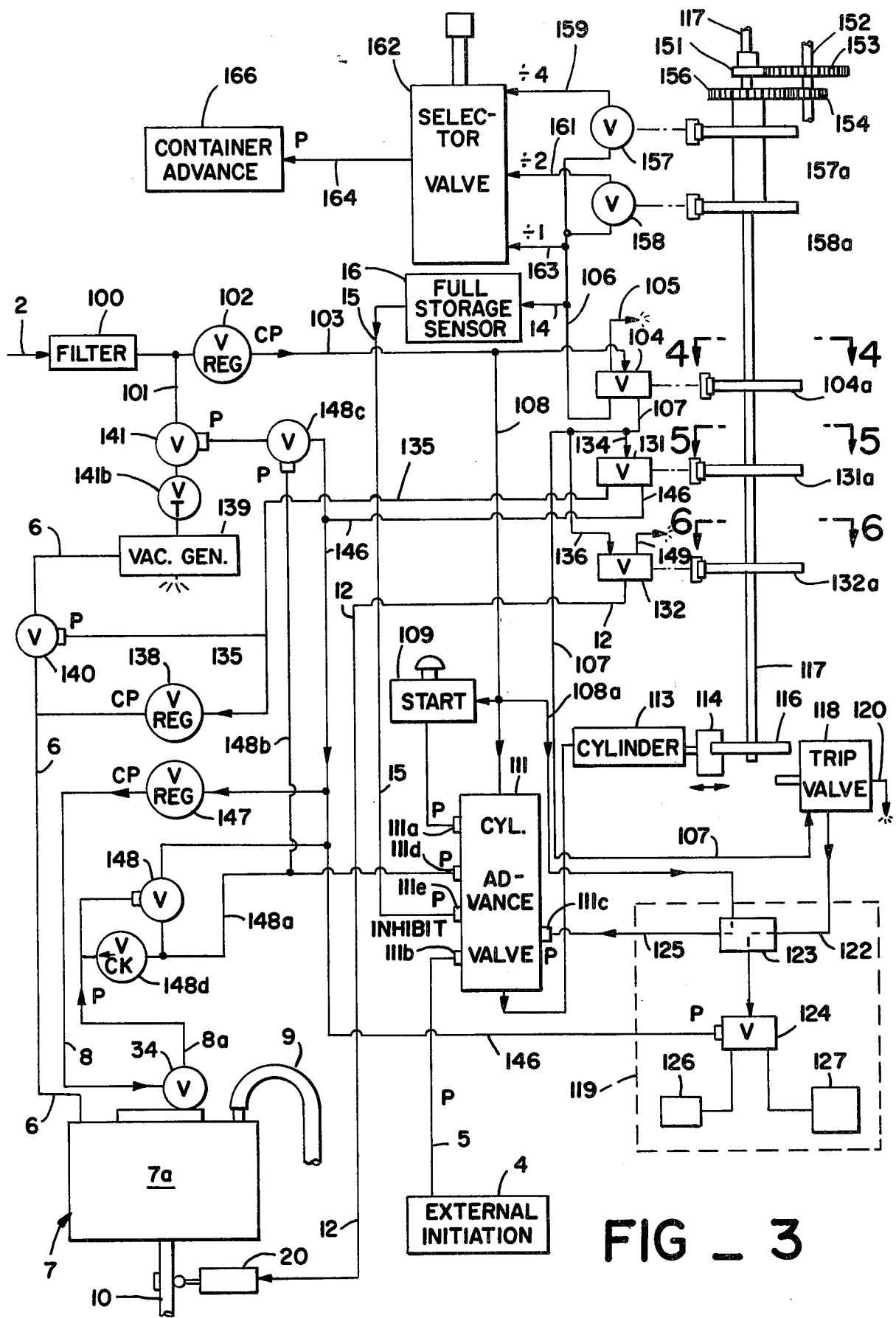
FIG_3

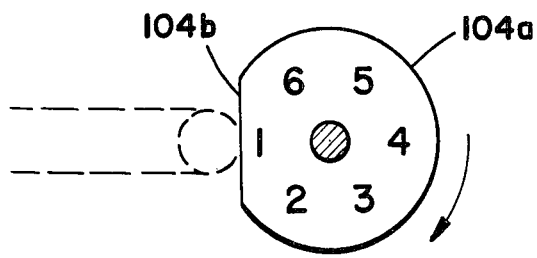
FIG_4
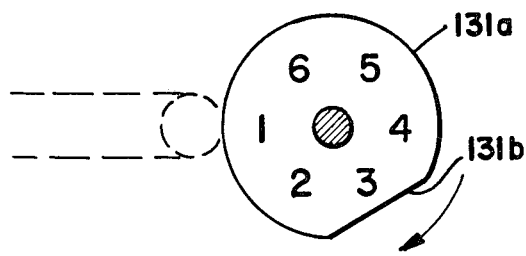
FIG_5
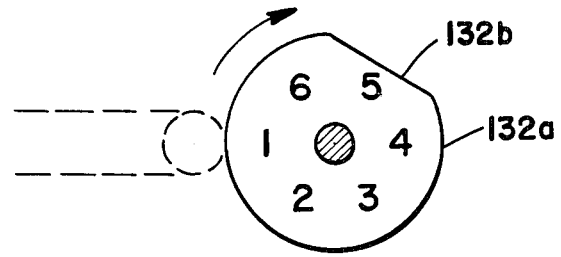
FIG_6
| | | PHASES | | | | |
|---|---|---|---|---|---|---|
| | 1 | 2 | 3 | 4 | 5 | 6 |
| | WAIT | PURGE | VACUUM/ FILL SENSE | MEASURE | DRAIN | POST-PURGE |
| SELECTOR LINE 106 PRESSURIZED | ▬▬ | | | | | |
| LATCH VALVE "ON" | | ▬▬▬▬▬▬▬▬▬▬▬▬▬▬▬▬▬▬▬▬▬▬ | | | | ▬▬ |
| VALVE 131 ON PURGE | | ▬▬ | | ▬▬▬▬▬▬ | ▬▬ | |
| VALVE 131 ON FILL SENSE/ VACUUM | | | ▬▬ | | | |
| PINCH VALVE "ON" | | ▬▬▬▬▬▬▬▬▬▬▬▬▬▬▬▬ | | | | ▬▬ |
| DURATION | IN-DEFINITE | 6 SEC. | FILL SENSE OR 30 SEC. | 6 SEC. | 6 SEC. | 6 SEC. |
FIG_7

EXPLOSION-PROOF FLOW SAMPLING APPARATUS

BACKGROUND OF THE INVENTION

This invention relates to apparatus and method for sampling liquid and solids-bearing liquid media such as sewage, particularly in explosive-atmosphere environments, by means of automatically functioning, pneumatically-operated apparatus.

In many flow streams it is desirable to monitor the contents of the flow by periodic sampling, as in the case of stream pollution control, sewage monitoring and industrial waste situations. Such monitoring is required by government in some cases. A variety of stream sampling devices have been proposed for these purposes. See, for example, U.S. Pat. Nos. 3,120,128; 3,438,262; 3,589,197; 3,750,477; and 3,795,347, and also British Pat. No. 720,161.

Increasing recognition of the explosive atmosphere hazard in sewage lines and other wastewater works has created a need for an explosion-proof sampling device. Electrically-operated devices must be either explosion proof or intrinsically safe (e.g., through use of extremely low voltage), to be operated in explosive atmospheres, or the device and/or the surrounding atmosphere must be purged with air. None of these methods provides absolute safety, and electrically-operated devices have proved dangerous. Several all-pneumatic samplers have previously been developed, but these devices have been underpowered, delicate, and undependable in sewage applications.

Of the above-cited patents, none shows a completely pneumatic sampler which avoids any reliance on electric circuitry, except U.S. Pat. No. 3,750,477, but the sampling apparatus disclosed in that patent is different from and without many advantages of the present invention. U.S. Pat. No. 3,795,347 does show a height-adjustable volume control tube as is included in the present invention described below, but the present sampler is all pneumatic and includes many other advantageous features not found in any of the apparatus of the cited patents.

SUMMARY OF THE INVENTION

The present invention overcomes the shortcomings, disadvantages, and dangers of prior sampling devices by the provision of a sufficiently powerful, entirely pneumatically operated and fully automatic flow sampler which may be positioned and used directly within an explosive atmosphere, such as a sewage conduit. The sampler draws liquid and accompanying solids from the sampled medium through a conduit to a quantimetric chamber within apparatus, measures a preselected quantity of sample material, returning the excess to the source, and dispenses the retained sample into a storage container. The apparatus may include a means for depositing a selected number of plural samples in each container and a full-storage sensing device for preventing the sampler from entering further sampling cyles once all storage facilities are full. Although the sampling apparatus may be very close to the sampled source, for example operating as a portable unit, it may also be at a distance from the source, communicating therewith through only a single intake line. In the usual installation the sampling device will be at a greater altitude than the sampled medium, although it can be adapted, if necessary, to operate at or slightly below the liquid level.

The quantimetric chamber device of the sampler is directed through the various phases of its cycles by a pneumatic controller which, by use of a single source of pressurized air (which may be a portable tank), supplies operating and pilot pressure to a number of valves, sensors, and other components including a cycle advancing cylinder, a timer and a vacuum generator. The controller has a number of components but yet is relatively simple in concept and operation, and utilizes trouble-free components, so that it is highly dependable in service. The controller is also structured to use a minimum of pressurized gas, thus permitting portable application and relatively infrequent compressed gas cartridge replacement.

It is therefore among the objects of the invention to provide an all pneumatic, amply powerful, reliable flow sampling system suitable for use with sewage and other explosive gas atmospheres, while providing for simple enough operation that the system can be used by unskilled personnel.

Other objects, advantages and features of the invention will become apparent from the following description of a preferred embodiment, taken in conjunction with the accompanying drawings.

BRIEF DESCRIPTION OF THE DRAWINGS

In the drawings:

FIG. 1 is a schematic representation showing the major components of the flow sampling system of the present invention;

FIG. 2 is a sectional elevation view of a measuring chamber associated with the system, including fill-sensing apparatus;

FIG. 3 is a diagrammatic representation of a pneumatic controller of the system, indicating the various pneumatic circuitry;

FIG. 4 is a view showing a valve-operating cam included in the controller, taken along the line 4—4 of FIG. 3;

FIG. 5 shows a second cam, viewed along the line 5—5 of FIG. 3;

FIG. 6 shows a third cam, viewed along the line 6—6 of FIG. 3; and

FIG. 7 is a chart which diagrams the positions of the main cam-operated valves during the several phases of operation in a cycle of the controller.

DESCRIPTION OF A PREFERRED EMBODIMENT

FIG. 1 shows a source of pressurized gas 1, which ordinarily contains air under pressure, unless some other gas is preferred for reasons of the particular environment in which the system is used. A conduit 2 leads from the gas source 1 to a controller 3 which directs the operation of the sampling system. A signal for starting the controller 3 and the cycling of the system may be provided by an external initiating apparatus 4 connected to the controller by a conduit 5. The initiator 4 may supply a pressure pulse for the purpose of starting the controller, and may include a pneumatic timer or other timing device, or a solenoid valve located outside the explosive atmosphere, such devices being well known in the art. If the initiator 4 operates on pressurized gas, a further conduit (not shown) may be provided from the controller or directly from the line 2 to the initiator.

Leading from the controller 3 to the upper position of a quantimetric chamber device 7 are a pressurizing-/evacuating conduit 6 and a pair of fill-sensing conduits 8 and 8a. Also entering the chamber device 7 is a sample intake hose 9. A pinch valve conduit 12 leads from the controller 3 to a pinch valve 13 at the base of the chamber device 7, engaging a drain conduit 10 that leads from the chamber to a storage container 11. A full storage sensor 16 may be provided, connected to the controller by conduits 14 and 15, for inhibiting any further cycling action of the controller when all storage facilities are full. This apparatus and its operation will be explained in more detail below.

THE CHAMBER APPARATUS

FIG. 2 shows a preferred embodiment of the quantimetric chamber device 7 in sectional elevation.

The device includes a base member 17 with a funnel-shaped interior. A mounting bracket 18 is secured to the bottom of the base element by suitable fasteners, and the mounting bracket also supports at its underside a pinch valve bracket 19 for the pinch valve 13. The valve 13 includes a spring-biased pneumatic cylinder 20 connected to the bracket 19 and positioned to constrict, when pressurized, the outlet conduit 10 which is of soft rubber or plastic material. The cylinder 20 relaxes pinching pressure when depressurized. Other types of on-off valve may be used here, but since the actuation of the valve is to be pneumatic, this simplified form is preferred. A particular advantage of this type valve is that it is less likely to become clogged by suspended solid materials in the samples being drained, than would any valve of conventional design.

Above the base member 17 is a preferably transparent cylinder 21, above which is a chamber top 22. Sealing the base 17 to the cylinder 21 and the chamber top 22 to the cylinder 21 are O-ring type seals 23, and the three components are all held together by two or more latch-straps 24.

The intake conduit 9 is shown entering the chamber 7a, through the top 22, but it may alternatively enter from the bottom through the base 17. In any event, there is preferably connected to the hose 9 a relatively rigid tube 25 which is vertically adjustable to act as a sample volume adjustment device. The tube 25 may be press-fit through the chamber top 22 in sealed engagement therewith, or an O-ring 25a may be provided for the sealing function and to exert a position-holding force on the tube 25. Volume calibrations may be provided on the exterior of the tube.

The pressurizing/evacuating conduit 6 enters the chamber 7a through a fitting 26 which communicates with the interior of a fill sensing tube 27. The interior of a sensor housing 28 is also in communication with the interior of the fill sensing tube 27 through a passage 30. Within the housing 28, sealed to its bottom surface, is a bellows or diaphragm member 29, the interior side of which communicates with the chamber 7a through an opening 31. A sensor plate 32 rests on the top of the bellows 29 and is connected to an arm 32a which extends to the exterior of the sensor housing 28. The interior of the housing 28 must be sealed from the atmosphere, and a flexible seal 33 such as an O-ring may be provided to seal the arm 32a with the housing. A fill sense valve 34 is mounted exteriorly on top of the housing 28 and is operatively connected with the arm 32a. The valve 34 is a simple on-off valve between the inlet and outlet lines 8 and 8a, biased toward its closed position (corresponding to a lower position of the plate 32 wherein the bellows 29 is essentially collapsed) by the weight of the plate 32 or by an internal spring (not shown).

Although the arrangement shown in FIG. 2 is preferred, the tube 27 may be considered a part of the conduit 6, with the passageway 30 amounting to a conduit connecting the line 6, upstream of the chamber 7a, with the interior of the sensor housing 28. Thus, the conduit 6 itself may extend down into the chamber, with a conduit 30 connecting an upstream part of the conduit 6 with the housing 28 interior. The preferred form shown, however, tends to insure that the sensed pressure differential is indeed due to the filling of the chamber and not to subtle line pressure differences in the line 6.

In operation, the quantimetric chamber device 7 cycles through a number of phases under the control of the controller apparatus 3, which is described in detail below. In the dormant or "wait" phase, the chamber interior 7a is empty, neither pressure nor vacuum is applied through the line 6, and the valve 34 is closed, since the bellows 29 is collapsed. Liquid is usually present in the bottom of the intake conduit 9, up to the level of the flow to be sampled, since the chamber 7a is open to the atmosphere through the line 6. The flexible drain conduit 10 is open, the cylinder 20 being vented and relaxed during the "wait" phase so that the conduit 10 retains its resiliency.

In the first active phase of the sampling cycle, the drain line 10 is pinched closed by the cylinder 20, and pressurized air is admitted to the chamber 7a through the line 6. This does not affect the position of the bellows 29 or the valve 34, since pressure on both sides of the bellows remains the same. The pressurized air purges the intake tube 9 so that the sample to be drawn is fully representative of the time period when it is taken. This purge phase is of a short duration, preferably about six seconds.

In the next phase of the cycle, which is a vacuum/fill sense phase, the drain conduit 10 remains closed by the pinch cylinder 20 and the line 6 becomes a vacuum line, evacuating the interior of the chamber 7a and drawing liquid and suspended solids up the intake conduit 9 and into the chamber. This phase continues until a full chamber is sensed by the apparatus 27 to 34, or until a back-up timing period expires, in the event the chamber does not fill, as discussed below.

Liquid is drawn into the chamber 7a until it reaches the bottom of the fill sensing tube 27 and rises slightly in the tube, at which point a pressure differential occurs between the two sides of the bellows 29. At this point, vacuum in the conduit 6 and in the tube 27 is slightly higher than vacuum prevailing in the chamber 7a above the sample level, since a slight hydraulic head difference exists. Approximately the same head difference will occur regardless of the height of the chamber device 7 above the flow being sampled, so that a consistent "full chamber" reference is available without need to rely on total chamber vacuum or conduit 6 vacuum (which vary with chamber height) as a fill reference. When this slight differential head occurs, the bellows 29 expands and causes the fill sense valve 34 to open, allowing low-pressure pilot air from the line 8 to flow into the line 8a. Through the controller apparatus described below, this quickly ends the fill phase and begins the measure phase, wherein the line 6 again becomes pressurized.

It should be noted that when the sampler is located significantly below its maximum operational height above the sample flow, the sample fluid surges in more quickly under the pull of the applied vacuum. In this situation, it is the difference between the dynamic effects of the water and air in the chamber, rather than the slight static head in the tube 27, which creates the sensed pressure differential. In this situation, and to some extent in all situations, liquid upon reaching the tube 27 surges upwardly to some extent in the tube 27. To prevent the liquid from entering the suction line 6 and an upstream vacuum generating apparatus described below, the tube may be provided with a bottom 27a with an opening 27b located to one side, not directly below the entry of the fitting 26. A baffle plate 27c may be provided to prevent splashing of the liquid into the fitting 26. Also, the tube bottom 27a may be funnel-shaped as shown, to assure proper draining of the tube 27. If solid material should rise to block the tube opening 27b, the dynamic effect of the sudden blockage will nonetheless trigger the fill sense mechanism at the proper time.

In the "measure" phase, air pressure on top of the sample surface forces some of the sample liquid back out the intake tube 9, or the liquid siphons out the tube 9, until the level reaches the bottom of the adjustable tube 25. At this point, and through the remainder of the approximately six-second measure phase, air from the line 6 merely passes through the tube 25 into the line 9. Thus, a preselected level and volume for the sample is effected. AT the end of this timed phase, the device 7 is shifted to a timed "drain" phase.

If desired, the measure phase can be eliminated, with the previous fill phase accomplishing the measuring step. If the sample volume need not be adjustable, the fill phase as described, with the apparatus illustrated, suffices to measure a generally consistent sample volume each cycle. If adjustable volume selection is desirable, the fill sense tube 27 can be made an axially, vertically adjustable estension of the conduit 6, slidable in the chamber top as is the illustrated tube 25. To serve as the passage 30, a branch conduit (not shown) from the conduit 6 can extend to the interior of the sensor housing 28. In either case, elimination of the measure phase enables elimination of the adjustable tube 25 on the intake line 9, and also economizes on cycle time and operating air, as will be seen in the discussion below of the controller apparatus 3. However, the inclusion of the measure phase is preferred because it produces greater sample volume accuracy in many situations. For example, different chamber filling speeds (due to different chamber heights) can cause inconsistent volume measurements if the fill sense tube 27 is relied upon alone for volume measurement.

In the drain phase the line 12 leading to the pinch cylinder 20 is vented, allowing the drain tube 10 to open and drain the measured sample into a storage container below. Pressurized air continues to flow into the chamber through the line 6, helping to force the sample, including soft, sticky solids often contained therein, through the drain tube and into the container. The friction of air passing through the sample intake hose 9, together with the fact that the end of the hose 9 is submerged, causes the pressure in the chamber to build up to about 2 to 5 p.s.i.g during the drain phase.

If non-solids-bearing liquids are to be sampled and it is desired to conserve compressed air, air flow through the line 6 can be stopped during the drain phase, with the line 6 vented, through apparatus associated with the controller 3.

At the end of the drain phase the apparatus is shifted to a final timed phase wherein the pinch cylinder 20 is again pressurized and pressurized air continues to flow through the line 6 into the chamber 7a. This is a "post-purge" phase for blowing out the intake tube 9 following the sample-taking operation. When this phase is finished, the sampling cycle is complete and returns the apparatus to "wait" mode described above.

THE CONTROLLER

The components of and the operation of the controller apparatus 3 are illustrated in the diagrammatic view of FIG. 3. High-pressure air (approximately 75 to 80 p.s.i.) enters the controller via the line 2 and passes through a filter 100. From there, the high-pressure air communicates with a line 101 and also through a pressure regulator 102 to a line 103, in which the air at a lower pressure which may be approximately 50 p.s.i. This line 103 is connected to a latch or "air-on" valve 104 which may connect the line 103 with either of two outlet lines 106 and 107. When the system is "off," i.e. not actively taking samples, the valve 104 is positioned to connect pressurized air with the line 106, which leads to a selector apparatus discussed below. The two-position valve 104 is double-acting in that when the line 107 is connected to the supply 103 and the line 106 is disconnected therefrom, the line 106 is connected to a vent 105 so that residual pressure in the line 106 is relieved. The line 107 need not be vented when disconnected.

Pressurized air from the line 103 also communicates through a line 108, regardless of the position of the latch valve 104, with a manual start valve 109, a 5-pilot cylinder advance valve 111, and a line 108a leading to a timing system described below, so that a constant air supply is available to these valves and components.

Prior to activation of the sampling portion of the controller 3, all of this apparatus is in a "wait" phase, with the line 107 disconnected from air pressure. To start a sampling cycle, the manual start valve 109 may be pushed, thereby supplying a pulse of air to a pilot 111a of the cylinder advance valve 111. A cycle may also be started automatically by the external initiation means 4, connected to a pilot 111b of the cylinder advance valve 111 by the pilot line 5. Both pilots are self-venting shortly after activation. In either case, one pilot 111a or 111b is energized to activate the cylinder advance valve 111, the sole purpose of which is to activate an advancing cylinder 113. Whenever a pilot of the cylinder advance valve 111 is energized (except an inhibit pilot 111e, discussed later), the valve 111 directs pressurized air from the regulated-air line 108 to the cylinder 113, which is spring-biased toward its normal retracted position. In response, the cylinder 113 pushes a tripper 114 outwardly to engage a tooth of a six-tooth ratchet gear 116, advancing an attached camshaft 117 by one-sixth of a turn. Pilots and pilot lines are indicated by the letter P in FIG. 3.

At the maximum extension of the tripper 114 in the stroke of the cylinder 113, it hits a trip valve 118 which opens to vent and reset a timing system 119 through a vent 120 so that the first phase of the sampling cycle (and each succeeding phase, as will be explained below) may be pneumatically timed. The cylinder 113 remains extended, with the trip valve 118 held open, until pilot pressure is relieved from the cylinder advance valve 111, which causes it to vent the cylinder 113. The time duration of the trip valve opening may be about ¼ second, to assure venting of the timing system 119. Alternatively, the cylinder 113 may include a self-venting device such as a bleed orifice.

The timing system 119 includes a pilot 111c connected to the cylinder advance valve 111; a line 122 leading from the trip valve 118 to a timer 123 including a flow restriction, leading to a volume selector 124; a pair of tanks 126 and 127 of different sizes for different timing periods; and the air supply line 108a and a pilot line 125, which are connected together at the end of the timing period by a pilot operated valve of the timer 123. This type of timing device is well known. When pressurized air from the line 122 passes through the restriction of the timer 123, pressure gradually builds up as the selected tank 126 or 127 fills up. When the system becomes pressurized to the required preselected extent, the pilot operated valve (not specifically illustrated) of the device 123 opens to abruptly apply full system pressure from the line 108a through the line 125 to the pilot 111c. The pressurized air in the line 122 is supplied from the timer line 107 leading from the latch valve 104, and these two lines are normally connected together through the trip valve 118. Their connection is interrupted only when the tripper 114 of the cylinder 113 hits the trip valve. This momentarily closes off the line 107 and at the same time vents the timer sysem, including the tank 126 and 127, through the timer 123, which includes a quick-exhaust check valve. This also closes the valve leading to the pilot line 125 and vents this line. The timing system 119 is vented and reset after each pressurization of the advancing cylinder 113 and the attendant one-sixth rotation of the camshaft 117.

To perform its venting and shutoff functions, the mechanically-actuated trip valve 118 may include well-known type on-off valves or a two-position valve, spring in each case to return to normal position when the cylinder 113 retracts. The normal position is with the timer air supply line 107 connected to the timer line 122.

When the camshaft 117 is rotated through one-sixth turn from its off position to its second position, this rotates cams 104a, 131a, and 132a operably connected to the latch valve 104, a purge/vacuum valve 131, and a pinch control valve 132, respectively. These valves are well-known type distributor valves. As shown in FIGS. 4, 5 and 6, each cam has only one flat, 104b, 131b, and 132b, located at one of the six positions of each cam, and the three flats are 120° apart. Instead of a flat, each cam could of course include a single lobe (not shown) in the one position, with the valve actuation mechanism correspondingly reversed. In this preferred mode, the "usual" position each valve assumes during the cycle is represented by the circular cam surface, with the shifted position of the valve represented by the flat. In FIGS. 4, 5 and 6 the cams are shown as they would be in a "wait" phase of the system, when the controller is not cycling through its phases and can be considered "off." The six positions of the cams are indicated by number in FIGS. 4, 5 and 6, with their direction of advancement indicated by arrows.

In the first position of the cams, or the "off" mode, the flat of the cam 104a serving the valve 104 is exposed, with the result that regulated air from the line 103 is directed through the selector line 106 rather than through the line 107. As noted above, the line 106 leads to a selector apparatus to be discussed later. Also in this "off" or "wait" phase the purge/vacuum valve 131 connects an inlet line 134 with a purge line 135, and the pinch control valve 132 connects an inlet line 136 with the pinch cylinder line 12. Of course, neither inlet line 134 or 136 is supplied with pressurized air during the "wait" phase, due to the position of the valve 104.

The positions of the valves 104, 131 and 132 during the six phases of a sampling cycle are graphically represented in FIG. 7. Dashed lines signify that the valve is in the indicated position, but with no effect, since inlet air is not being supplied. The solid bars signify that the valve is in the position shown and operative.

When the camshaft 117 rotates through its initial one-sixth turn, only the latch valve 104 changes its position, shifting air supply away from the line 106 and into the line 107 leading to the timing system 119 and to the other camoperated valves 131 and 132. Thus, pressurized air is supplied to the purge line 135 and the pinch line 137. A timing cycle is begun, and since the pilot of the volume selector 124 is not supplied with pressure, the smaller volume tank 126 is used for the timing, preferably providing a timed cycle of about six seconds.

In this first phase, a purging phase as discussed above, the purge line 135 passes air through a pressure regulator 138, which reduces outlet pressure to about 5 – 10 p.s.i. This supplies sufficient pressure and flow to the line 6 to purge the fluid intake line 9 of the sampling chamber 7 discussed above. The line 6 is also connected to a vacuum generator 139, but a pilot-operated valve 140 in the line 6 closes during purging, its pilot being connected by a line 142 to the purge air supply line 135. This prevents the flow of purge air through the vacuum generator, which has an open of purge air through the vacuum generator, which has an open exhaust.

Meanwhile, the pinch cylinder 20 is supplied with pressurized air by the pinch control valve 132 and the pinch line 12, pinching closed the sample drain line 10 so that purging of the sample intake line 9 can take place.

During the purge, the timer line 107 supplies pressurized air through the line 122 into the timing system. The air flows through the restriction 123 and the volume selector 124 to the smaller timing tank 126, which is normally connected, and an approximately six-second delay occurs before the pilot 111c of the cylinder advance valve 111 reaches actuation pressure. When this pilot is actuated, the valve 111 supplies another short burst of air to the advancing cylinder 113, ending the purge phase, causing the camshaft 117 to advance another one-sixth turn to its next (third) position, and again momentarily venting the timer system via the line 128 while shutting off the timer supply air from the line 107. With the retraction of the cylinder 113, a new timing cycle begins. The approximately six seconds of purge is sufficient, with the 5 – 10 p.s.i. of purge air applied, to purge the sample intake line 19.

In the third camshaft position, the latch valve 104 and the pinch valve 131 remain in their same positions, so that the sample drain line 10 from the sampling chamber is maintained closed. However, the cam 131a serving the purge/vacuum valve 131 reaches its flat, so that air pressure from the inlet line 134 is shifted from the purge line 135 to a fill sense/vacuum line 146, and the fill phase begins.

The line 146 immediately supplies pilot air to the volume selector valve 124 of the timing system 119, so that the larger volume tank 127 is selected, representing a timing of about 30 seconds for this phase. This is merely a backup timing for this phase in case the sampling chamber 7a does not fill for some reason. In normal operation, the phase ends when the chamber is sensed to be full, which is a much shorter period than 30 seconds.

The purge line 135 is now shut off at its upstream end by the valve 131. The on-off valve 140 in the line 6 relaxes to its normal open position due to the lack of pilot pressure; the pilot pressure vents through the purge pressure regulator 138 and the line 6. During this phase the line 6 becomes a vacuum line, as explained below.

The fill sense/vacuum line 146 supplies pilot air to a high-flow vlave 141 via a pilot line 141a. The valve 141 is connected to high-pressure air (which may approximately 75 – 80 p.s.i.) upstream of the regulator 102. The pilot pressure in the line 141a opens the high-flow valve and causes a large, rapid flow of air to pass through the vacuum generator 139 to be exhausted to the atmosphere. The vacuum generator 139 preferably comprises a well-known venturi-type vacuum generating device, with the line 6 connected at the maximum vacuum area. A manually-operable variable-flow or throttle valve 141b may be included downstream of the valve 141 to control vacuum output magnitude. However, the vacuum generator may also be a vacuum pump driven by a pressurized fluid-driven motor or even an external, separate source of vacuum, in which case pressurized air from the line 101 would not be required.

The suction in the line 6 draws on the chamber interior and causes liquid or slurry from the sampled medium to flow up through the intake line 9 and into the chamber, as discussed in connection with FIG. 2.

Meanwhile, the fill sense/vacuum line 146 is also supplying pressurized air through a pressure regulator 147, which further reduces pressure to about 1 – 2 p.s.i., to the line 8 leading to the fill sense valve 34. This valve is normally closed, preventing flow through the return line 8a, but opens when the fill sensing bellows 29 of the chamber apparatus 7 fills, as discusssed above. The reason for the low level of pressure is that the bellows 29 and the fill sense valve 34 are relatively sensitive, being set to sense a relatively small pressure difference in the chamber.

With respect to the sampling chamber apparatus 7, the operation of the fill sensing device has already been discussed. As previously explained, the filling of the chamber activates the bellows 29 and opens the valve 34, at which point the liquid level in the chamber has reached the bottom of the fill sensing tube 27 and some liquid has entered the tube 27. The next step, of course, is to move the liquid level back down, by directing some of the liquid back out the intake line 9, until the liquid level reaches that of the bottom of the adjustable tube 25. This is accomplished in the coming "measuring" phase.

When pressurized air flows into the line 8a from the fill sense valve 34, it supplies pilot pressure to an amplifier valve 148, opening the valve. This has the effect of supplying higher pilot pressure (the normal system pressure of about 50 p.s.i.) through a pilot line 148a to another pilot 111d of the cylinder advance valve 111. Thus, another pressurized air is again introduced to the cylinder 113, advancing the camshaft to its fourth position and (normally) aborting the 30-second timer cycle before activation pressure builds up in the pilot 111c. This resets the timing system 119 for the "measure" phase. The suction applied to the chamber may be made to shut off immediately, applied to the chamber may be made to shut off immediately, without waiting for the phase shift to be completed, by the provision of a second pilot line 148b connected to the valve 148a, as shown, and to a pilot-operated shut off valve 148c in the pilot line 141a leading to the high-flow valve 141. As soon as the valve 148 is opened by the the fill sensing assembly, the resulting flow of pilot air closes the valve 148c, so that vacuum quickly ceases. This stops the sample inflow slightly earlier than the completion of the phase shift, so that sample liquid is not drawn into the line 6. The lines 148a and 148b are vented after the phase shift by apparatus assoiacted with the valve 148.

It has been found that jitter or flutter can occur with the fill sense system described, prior to the phase shift. As the turbulent water surface in the chamber 7a rises to the bottom of the sensing tube, the fill sense valve 34 often flutters on-off-on-off for a short time, not supplying a steady signal to advance the camshaft or shut off vacuum until the sample is often undesirably high in the tube 27 or even into the line 6. To eliminate this flutter and cause a prompt phase shift, a check valve 148d may be installed as shown between the line 148a and the fill sense low-pressure pilot line 8a, allowing flow only from the line 148a to the line 8a. Thus, as soon as a sufficient pulse of pilot air in the line 8a opens the valve 148, higher pressure air admitted to the line 148a feeds back to the pilot of the valve 148 to keep it open so that suction is stopped and the phase is shifted.

If for some reason a chamber fill is not sensed within 30 seconds, as for example if the intake conduit 9 becomes clogged or insufficient liquid is available in the medium to be sampled, then the 30-second timer cycle advances the controller to the next phase without fill sense. The remainder of the cycle can be completed without appreciable waste of pressurized air, with the controller returned to its "wait" mode.

It should be understood that other pneumatically operated apparatus can be employed to sense the filling of the chamber 7a. For example, an external device such as a sensor of the total weight of the chamber apparatus can be used instead of the differential pressure sensing apparatus shown and described. Such a device would open a valve similar to the valve 34 upon sensing the weight of the full chamber 7a. The device may even be used as a substitute for both the described fill sensing apparatus and the succeeding measure phase, particularly if the substitute device is adjustable as to the sample volume. However, the apparatus described herein is preferred.

In the fourth camshaft position, the measure phase, the cams 104a and 132a continue to maintain the latch valve 104 and the pinch control valve 132 in their previous positions. However, the purge/vacuum cam 131a moves off its flat, causing the valve 131 to switch the flow of pressurized air from the fill sense/vacuum line 146 back to the purge line 135. A six-second timing begins.

The measure phase is similar to the purge phase described above. Pressurized air, reduced to a somewhat lower pressure via the regulator 138, is supplied through the line 6 to the interior 7a of the sampling chamber device 7. This pushes the liquid level down to the bottom of the adjustable inlet tube 25, or allows it to siphon down to this level in the usual case of an elevated chamber device 7. In any event, once the liquid or slurry level backs down to this point, representing the desired measure of the sample, additional air entering through the line 6 during the remainder of the six-second measure phase merely passes out the intake conduit 9. The phase is ended by the timer in the usual manner, and shifted to the "drain" phase, on the fifth camshaft position. Meanwhile, the fill-sensing bellows 29 relaxes, closing the fill sense valve 34, and the fill sense pilot line 8a is vented preferably through apparatus included in the amplifier valve 148, such as a bleed orifice.

In the drain phase, the fifth camshaft position, the purge/vacuum valve 131 remains in its previous position, leaving the purge line 135 connected to the air supply, and low-pressure purge air continues to flow through the chamber 7a. Also, the latch valve continues in its active position. However, the pinch control valve cam 132a reaches its flat and shifts the valve 132 so that the pinch line 12 is disconnected from the inlet line 136 and connected to a vent outlet 149. The pinch cylinder 20 relaxes and the drain line 10 opens, draining the sample into the storage vessel. This phase also lasts 6 seconds, allowing ample time to drain the chamber, since the volume selector 124 of the timing system is not activated.

As mentioned above, it may be desirable to shut off air flow through the line 6 during the drain phase to save compressed air, in the event that non-solids-bearing liquids are to be sampled. To this end, a pilot-operated valve (not shown) may be included in the line 6 between the pressure regulator 138 and the chamber 7a, with its pilot connected to the pinch line 12. This pilot would be operative to hold the valve open when pressurized by the line 12 (all active phases except drain), and to vent the line 6 when pilot pressure is removed. Such venting would be desirable for best draining.

At the end of the drain phase, the camshaft 117 is rotated ahead to a sixth position, for a "post-purge" phase. This 6-second phase is similar to the first purge phase, with the pinch cylinder 20 again activated to close the drain line 10. The purpose of the post-purge phase is to purge or blow out the fluid intake conduit 9 following the active sampling portion of the cycle. If clogging materials prevent the filling of the chamber 7a during the fill phase, they will be blown back out the intake conduit 9 during the measure and post-purge phases.

At the end of the post-purge phase, the camshaft 117 is rotated ahead to its original position, with the latch valve 104 shifted to its "off" position. This reconnects the selector line 106 with the air supply. Air pressure is now disconnected from the purge/vacuum valve 131, the pinch control valve 132, and all lines and apparatus downstream of these valves, including the timing system 119. The result is a quiescent "wait," until another pulse is received from either the manual start valve 109 or the external initiating apparatus 4.

As mentioned above, the pinch line 12 is vented during the "wait" period, so that the flexible drain tube 10 is not squeezed for long periods of time. This venting occurs by backflow through the valve 132 and the lines 136, 107 and 134, through the valve 131 and the line 135, from which the pressure regulator 138 rapidly bleeds the pressure down.

If the controller of FIG. 3 is for use with multiple storage containers, additional apparatus is required to control the mechanism employed for distributing samples among the containers. Common types of distribution mechanism include a rotating spout or a linear advance. Such devices may be obtained which require only a single pneumatic pulse to operate. Such a pulse is available from the line 106 leading out of the latch valve 104. This line may be connected directly to the distribution mechanism.

However, in some applications it is desirable to place several samples in each container before advancing to the next. This function may be provided for by the apparatus diagrammatically illustrated at the top of FIG. 3. This is one preferred example of such apparatus; other forms may also be employed.

In the apparatus illustrated, the camshaft 117, which rotates one complete turn during each sampling cycle, drives a small gear 151, which in turn drives a countershaft 152 via a larger gear 153. A smaller gear 154 on the shaft 152 drives a large gear 156 which rotates on, but is not affixed to, the shaft 117. The gear reduction is such that the gear 156 rotates at one-fourth the rate of the shaft 117 and first gear 151. Affixed to and rotating with the gear 156 are a pair of cams 157a and 158a, each of which mechanically controls a valve 157 or 158, respectively. The cam 157a includes only one flat (not shown) while the other cam 158a includes two 180°-opposite flats. Each of these flats becomes exposed to shift the corresponding valve to its open position only when the sampling apparatus is in an "off" or "wait" mode, and not every time this mode occurs. Thus, the flat of the cam 157a comes up at the completion of every fourth sampling cycle, while a flat of the cam 158a comes up at the completion of every second sampling cycle. The valves 157 and 158 are normally closed; they open when a cam flat appears. Each time one or both of the valves 157 and 158 opens, pressurized air is available to them through the line 106, since air flows through this line whenever the remainder of the apparatus is "off" (see bar graph of FIG. 7).

The downstream side of each valve 157 and 158 is connected, via lines 159 and 161, to a three-position, manually operable selector valve 162. In addition, a line 163 connects the line 106 directly with the selector valve 162. Therefore, the manually-operable selector valve 162 may be positioned to accept a pulse of pressurized air from the line 106 at the completion of every sampling cycle; at the completion of every second sampling cycle; or at the completion of every fourth sampling cycle. The selected pulse is sent through a line 164 to a container advance mechanism 166, which is operable to advance to the next empty container in response to such a pulse. Each container in which samples are deposited from the chamber device 7 would thereby receive either one sample, two samples, or four samples. Obviously, this apparatus or other suitable apparatus can be adapted to provide for any number of samples to be deposited in each container.

Whenever a container advance is completed, the system including the controller of FIG. 3 is ready for another sampling cycle. The next cycle may be initiated by the external initiator 4 upon any desired basis, such as time of day, in response to flow conditions, etc. When another cycle is begun, the line 106 and all the lines 159, 161, 163, and 164 are vented via the vent line 105, by the shifting of the valve 104. As described above, the valve 104 connects the line 106 to the vent line at all times during the five active sampling phases. Therefore, pilot pressure is relieved from the container advance 166, and it is reset for the next cycle completion.

It may also be desired, whether or not the selector valve 162 and associated apparatus is included, that the sampling apparatus automatically cease operation when all available sample storage is filled. To this end, the full storage sensor 16 indicated in FIGS. 1 and 3 may be included in the system, connected by the line 14 to the "wait" phase air supply line 106, so that air pressure is provided to the sensor 16 at the completion of each sampling cycle. The full storage sensor may take a variety of forms, such as a weighing device when a single storage container is employed, or a device for sensing a full cycle of movement of a distributing apparatus, in the case of multiple sample storage containers. In any event, the sensor 16 may be operable to admit pressurized air from the line 14 to the pilot line 15 upon sensing of the full condition. The line 15 leads to a pilot 111e of the cylinder advance valve 111, but this pilot is set to inhibit cycle operation when pressurized, rather than initiating it.

As long as pilot pressure remains in the inhibit pilot 111e, none of the other pilots of the valve 111 can cause the advancing cylinder 113 to activate, even if pilot pressure reaches them. The inhibit pilot 111e may, for example, shut off air from the line 108 into the valve 111 as long as it is pressurized. It may, therefore, comprise a common type pilot-operated valve, with the valve operated by the pilots 111a through 111d located downstream. Thus, neither the manual start valve 109 nor the external initiator 4 can start a cycle as long as all sample storage facilities are full. However, once the full condition is manually corrected and reset, with the inhibit pilot line 15 vented, a sampling cycle may be started in the usual manner. The venting of the line 15 may be accomplished by the provision of manual venting apparatus at the full storage sensor 16 (not shown), or automatic venting apparatus associated with the sensor, operable to momentarily vent the line 15 whenever the sensor is actuated, then released (not shown). The release would occur whenever the full condition is removed. Such venting apparatus can employ well-known type valving equipment.

If it is desired to fill a series of containers in continuous cycling, pneumatic apparatus (not shown) may be provided between the line 106 and the external initiator 4, or directly between the line 106 and the cylinder advance valve 111, to start a new cycle whenever a cycle is completed. In the latter case the linking apparatus may take the form of an additional pilot on the valve 111, connected into the line 106. Container advance may still occur when called for, and cycling is inhibited whenever full storage is sensed. A valve (not shown) may be provided in the added pilot line or in the external initiator 4 so that either continuous cycling or normal one-cycle operation may be manually selected. The occurrence of single cycles is, of course, controlled by the manual start valve 109 or the external initiator 4, as discussed above.

The above described preferred embodiment provides flow sampling apparatus which is explosion proof because of its entirely pneumatic operation, which is fully automatic in its cycling operations, and which may be produced in portable form and placed directly in a sewer line or other facility in which samples are to be taken. Some variations to the described embodiment may be made, such as the use of sequential logic instead of the illustrated camshaft arrangement, which is preferred because it is more easily understood and operated by less skilled personnel. Similarly, certain phases of operation of the sampling cycle may be eliminated, the most essential phases being the fill phase and the drain phase. These and other changes to this preferred embodiment will be apparent to those skilled in the art and may be made without departing from the spirit and scope of the following claims.

I claim:

1. An explosion-proof flow sampling apparatus for taking samples from liquids which may contain solids, comprising:
   a sealed chamber;
   an intake conduit connecting the chamber with the flow to be sampled;
   a source of vacuum connected to the chamber;
   a drain conduit at the bottom of the chamber for draining a sample into a storage container below, said drain conduit including a shutoff valve;
   a tube leading downward from the top of the chamber to a level approximately representing a full chamber, said source of vacuum communicating with the chamber through the tube;
   means for sensing a predetermined pressure difference between the interior of the tube and the remainder of the chamber above the level of the liquid; and
   pneumatically-operated controller means operably connected to said sources of pressure and vacuum, to said drain conduit shutoff valve, and to said sensing means, including means for activating the source of vacuum to exert suction on the chamber while holding closed the shutoff valve to draw sample material into the chamber through the intake conduit until the sensing means senses said predetermined pressure difference; means for terminating the vacuum after the sensing of said pressure difference; and means for subsequently opening the shutoff valve to drain the sample through the drain conduit to the storage container.

2. The apparatus of claim 1 which further includes a source of pressurized gas connected to the chamber, and wherein the controller means inludes means for supplying pressurized gas from the gas source to the chamber for a predetermined period while holding closed the drain conduit shutoff valve, prior to activating the source of vacuum, to thereby purge the intake conduit of fluid from the flow before drawing a sample.

3. The apparatus of claim 2 wherein the controller means further includes means for supplying pressurized gas from the gas source to the chamber for a predetermined period while holding closed the drain conduit shutoff valve, subsequent to the draining of the sample, to purge the intake conduit of remaining fluid.

4. The apparatus of claim 1 wherein the intake conduit includes a chamber end portion with an open end of adjustable height in the chamber, below the level of said tube, and wherein the controller means includes means for relieving vacuum in the chamber for a predetermined period following the termination of vacuum, with the drain conduit shutoff valve closed, so that sample material siphons back out of the chamber through the intake conduit until the level of the open end is reached.

5. The apparatus of claim 1 wherein the intake conduit includes a chamber end portion with an open end of adjustable height in the chamber, below the level of said tube, and wherein the controller means includes means for supplying pressurized gas from the gas source to the chamber for a predetermined period following the termination of vacuum, with the drain conduit shutoff valve closed, so that sample material flows back out of the chamber through the intake conduit until the level of the open end is reached.

6. The apparatus of claim 1 wherein said sensing means comprises a flexible diaphragm movable in response to relative pressure changes on its opposite sides, one side being in communication with the interior of said tube and the other side being in communication with the remainder of the chamber, and pneumatic valve means connected to the controller means for shifting from one position to another in response to a predetermined amount of movement of the diaphragm.

7. The apparatus of claim 6 wherein said pneumatic valve means is connected to a supply of low-pressure gas and to an outlet pilot line during the filling of the chamber, and opens the low-pressure gas supply to the pilot line in response to said diaphragm movement.

8. The apparatus of claim 7 wherein the controller means includes a plurality of pneumatic valves operated by cams mounted on a camshaft, each position of which corresponds to a particular phase of operation of the chamber, a pneumatic cylinder operably connected to incrementally rotate the camshaft in response to a pulse of pressurized gas supplied to the cylinder, and means for supplying such a pulse of pressurized gas in response to the flow of low-pressure gas into said outlet pilot line.

9. The apparatus of claim 1 wherein said drain conduit is a flexible tube and said shutoff valve comprises a pneumatic cylinder and pinching means for pinching closed the drain conduit in response to pressurization of the cylinder, said cylinder being connected by a pneumatic line to the controller means.

10. The apparatus of claim 1 which further includes a source of pressurized gas and wherein said pneumatically operated controller means includes a venturi-type vacuum generator connected to the chamber and selectively connectible by the controller means to the source of pressurized gas for activating said source of vacuum when the chamber is to be filled.

11. The apparatus of claim 1 which further includes a source of pressurized gas and wherein the controller means includes a plurality of pneumatic valves operated by cams mounted on a camshaft having a plurality of positions, each of which corresponds to a phase of a sampling cycle of the chamber, including at least a fill phase and a drain phase, a pneumatic cylinder operably connected to incrementally rotate the camshaft from phase to phase in response to a pulse of pressurized gas supplied to the cylinder, a cylinder advance valve connected to the pressurized gas source and to the cylinder for supplying such pulses, and a plurality of pressure-sensitive pilots associated with the cylinder advance valve, one pilot operable during the fill phase to feed a pressure pulse to the cylinder in response to the sensing of said predetermined pressure difference, thereby rotating the camshaft to shift the controller means and the chamber out of the fill phase and discontinue suction on the chamber, and another pilot operable to start a cycle.

12. The apparatus of claim 11 wherein the controller means further includes pneumatic timing means for providing a measured period longer than that normally required for filling of the chamber, including a third pilot operable to feed a pressure pulse to the cylinder at the end of said measured period if said predetermined pressure difference has not been sensed.

13. The apparatus of claim 11 wherein the sampling cycle of the chamber further includes a purge phase for purging the intake conduit prior to the fill phase, and the controller means includes means for supplying pressurized gas from the gas source to the chamber during said purge phase for a measured time period while maintaining the drain conduit shutoff valve closed, said controller means including pneumatic timing means and a third pilot associated with the cylinder advance valve and the timing means and operable to feed a pressure pulse to the cylinder at the end of said measured time period to end the purge phase.

14. The apparatus of claim 13 wherein the sampling cycle of the chamber further includes a measure phase between the fill phase and the drain phase, said intake conduit including a chamber end portion with an open end of adjustable height in the chamber, below the level of said tube, and said controller means including means for relieving vacuum in the chamber for said measured time period while maintaining the drain conduit shutoff valve closed, so that sample material siphons back out of the chamber through the intake conduit to the level of the open end, said third pilot being operable to feed a pressure pulse to the cylinder at the end of said measured time period to end the measure phase.

15. An explosion-proof flow sampling apparatus for taking measured samples of liquids with or without solids therein, comprising:
 a sealed measuring chamber having an intake conduit connecting the chamber with the flow to be sampled, a drain conduit at the bottom of the chamber for draining a sample into a storage container below, and a shutoff valve in the drain conduit;
 means for sensing a condition wherein the chamber is filled to a preselected extent;
 a source of pressurized gas connectible to the chamber;
 a source of vacuum connectible to the chamber above the intended fluid level; and
 pneumatically-operated controller means connected to said sources of pressurized gas and vacuum, to the drain conduit shutoff valve and to the sensing means, including means for activating the source of vacuum to exert suction on the chamber while holding closed the shutoff valve to draw sample material into the chamber through the intake conduit, means for terminating the vacuum upon the sensing of said filled condition, and means for subsequently opening the shutoff valve to drain the sample through the drain conduit, said activating, terminating, and opening means including a plurality of pneumatic valves connected to the gas source and operated by cams mounted on a camshaft, each position of which corresponds to a particular phase of operation of the chamber, a pneumatic cylinder operably connected to incrementally advance the rotational position of the camshaft in response to a pulse of pressurized gas supplied to the cylinder, and means for supplying such a pulse from the gas source to the cylinder at the end of each phase of operation of the chamber.

16. The apparatus of claim 15 wherein said source of vacuum includes a venturi-type vacuum generator connected to the chamber and selectively connectible by the controller means to the gas source for activating the source of vacuum when the chamber is to be filled.

17. A method for taking samples of solids-bearing liquids using a chamber having an inlet communicating with the material to be sampled, a bottom outlet including a pneumatic pressure-operated valve, and a conduit leading to a control opening near its top, by fully pneumatic means, comprising the sequential steps of:

applying vacuum to the control opening while also supplying pressurized air to the pneumatic pressure-operated valve to maintain the valve closed, thereby drawing in sample material to the chamber;

pneumatically determining when the chamber is filled to a preselected level;

discontinuing vacuum to the control opening when a filled chamber is determined; and discontinuing the supply of pressurized air to the pneumatic pressure-operated valve to open the valve and drain the sample into a container below.

18. The method of claim 17 wherein the pneumatically determining step comprises continuing the vacuum application until the sample material reaches the control opening, then sensing a pressure differential between the interior of the conduit leading to the control opening and the interior of the chamber above the sample.

19. The method of claim 18 wherein the pneumatically determining step further includes opening a pilot pressure-supplying valve in response to the sensing of the pressure differential.

20. The method of claim 17 which further includes, prior to the vacuum-applying step, the step of supplying pressurized air to the control opening while also supplying pressurized air to the pneumatic pressure-operated valve to maintain the valve closed, for a measured time period.

21. The method of claim 17 wherein the vacuum-applying step comprises supplying pressurized air to a venturi-type vacuum generator connected to the control opening.

* * * * *